United States Patent
Shemer et al.

(10) Patent No.: US 9,155,458 B2
(45) Date of Patent: Oct. 13, 2015

(54) PORTABLE DEVICE FOR CERVICAL INSPECTION COMPRISING GROUPS OF LIGHT-EMITTING DIODES

(75) Inventors: Isaac Shemer, Stockholm (SE); Elisabeth Wikstrom Shemer, Stockholm (SE); Matthew Volsky, Stockholm (SE)

(73) Assignee: GYNIUS AB, Stockholm (SE)

( * ) Notice: Subject to any disclaimer, the term of this patent is extended or adjusted under 35 U.S.C. 154(b) by 402 days.

(21) Appl. No.: 13/698,983

(22) PCT Filed: May 18, 2011

(86) PCT No.: PCT/SE2011/050628
§ 371 (c)(1),
(2), (4) Date: Nov. 19, 2012

(87) PCT Pub. No.: WO2011/146007
PCT Pub. Date: Nov. 24, 2011

(65) Prior Publication Data
US 2013/0066165 A1    Mar. 14, 2013

(30) Foreign Application Priority Data

May 18, 2010  (SE) .................................. 1050494-2

(51) Int. Cl.
*A61B 1/06*    (2006.01)
*A61B 1/303*   (2006.01)
*A61B 5/00*    (2006.01)

(52) U.S. Cl.
CPC ................. *A61B 1/06* (2013.01); *A61B 1/0607* (2013.01); *A61B 1/0638* (2013.01);
(Continued)

(58) Field of Classification Search
CPC .. A61B 17/42; A61B 17/4225; A61B 5/4331; A61B 5/4306; A61B 5/4318; A61B 1/32; A61B 1/0638; A61B 1/0623; A61B 1/0607; A61B 1/06
See application file for complete search history.

(56) References Cited

U.S. PATENT DOCUMENTS 3,910,701 A    10/1975  Henderson et al.
5,036,853 A     8/1991  Jeffcoat et al.
(Continued)

FOREIGN PATENT DOCUMENTS

EP    0019262    11/1980
GB    1542702     3/1979

OTHER PUBLICATIONS

International Search Report and Written Opinion received for PCT/IB2013/002726, dated Mar. 3, 2014, 12 pages.
(Continued)

*Primary Examiner* — Eduardo C Robert
*Assistant Examiner* — Julianna N Harvey
(74) *Attorney, Agent, or Firm* — ARC IP Law, PC; Joseph J. Mayo

(57) ABSTRACT

A portable device for cervical inspection, comprising a plurality of light-emitting diodes comprising a first light-emitting diode group and a second light-emitting diode group, wherein the first light-emitting diode group emits light within a first wavelength range upon operation, and the second light-emitting diode group emits light within a second wavelength range upon operation, wherein the first wavelength range comprises a sub-range of wavelengths shorter than the wavelengths of the second wavelength range, and the second wavelength range comprises a sub-range of wavelengths longer than the wavelengths of the first wavelength range, the portable device further comprising a controller provided for a control of the luminous intensity of the second light-emitting diode group from a first intensity to a second intensity, lower than the first intensity, such that a preferred color rendering for the visual examination of the cervix may be provided.

30 Claims, 4 Drawing Sheets

(52) U.S. Cl.
CPC ............ *A61B 1/0676* (2013.01); *A61B 1/0684* (2013.01); *A61B 1/303* (2013.01); *A61B 5/4331* (2013.01); *A61B 5/0084* (2013.01)

(56) References Cited

U.S. PATENT DOCUMENTS

| | | | |
|---|---|---|---|
| 6,110,106 A * | 8/2000 | MacKinnon et al. | 600/181 |
| 6,496,718 B1 | 12/2002 | Lonky | |
| 2002/0065468 A1 * | 5/2002 | Utzinger et al. | 600/476 |
| 2002/0139920 A1 * | 10/2002 | Seibel et al. | 250/208.1 |
| 2002/0161282 A1 * | 10/2002 | Fulghum | 600/160 |
| 2004/0111031 A1 | 6/2004 | Alfano et al. | |
| 2005/0194876 A1 | 9/2005 | Shimada et al. | |
| 2006/0215406 A1 | 9/2006 | Thrailkill | |
| 2006/0241347 A1 * | 10/2006 | Whitehead | 600/146 |
| 2010/0016668 A1 | 1/2010 | Gal | |
| 2011/0222164 A1 | 9/2011 | Seo et al. | |
| 2011/0299174 A1 | 12/2011 | Obrebski | |

OTHER PUBLICATIONS

International Search Report received for PCT/SE2011/050628 dated, Aug. 22, 2011, 5 pages.

* cited by examiner

PORTABLE DEVICE FOR CERVICAL INSPECTION COMPRISING GROUPS OF LIGHT-EMITTING DIODES

FIELD OF THE INVENTION

The present invention relates to a portable device for inspection of body cavities.

BACKGROUND OF THE INVENTION

Cervical cancer is one of the most common types of cancer affecting women, the disease being the cause of approximately a quarter of a million deaths every year. Furthermore, for women in the developing countries, it is the leading cause of cancer related mortality.

In the developed countries, there has been a 75% decrease in incidence and mortality from cervical cancer over the past 50 years. Most of this decrease is attributed to cervical cytology screening which helps keep cervical cancer rates relatively low. The screening programs are often effective as women in the developed countries may easily access health facilities for regular Pap tests, i.e. tests for the detection of pre-malignant and malignant processes in the cervix. If a cancer is found, it may be successfully treated while still in the early stages. Thus, early detection and diagnosis can save lives and moreover reduce the burden on the national healthcare system.

In the developing countries, however, the cervical cytology screening is not applicable in low-resource settings. Hospitals in many of the poor countries do not have the resources for this kind of gynecological examination of women. Furthermore, women in some developing countries do not even have access to gynecological investigation whatsoever, due to inferior transportation facilities, wars, or similar obstacles that makes it difficult, or impossible, to get adequate gynecological examinations.

Thus, there is a need to further develop colposcopes or devices of the kind such that more women, especially in the third world, may have access to visual cervical-screening for early detection of cervical pathologies.

For a visual examination of a cervix via colposcopy, the experience of the examiner, e.g. a doctor or a nurse, performing the examination is of vital importance. The experience is gained through numerous examinations using a conventional colposcope which is, therefore, the conventional training tool for gynecologist for visual detection of cervical lesions. For this reason, a reproduction of the lighting of the conventional colposcope is important for the purpose of cervical inspection. For an examiner examining the cervix, the detection of healthy and unhealthy cervical tissue therefore puts high demands on the lighting and the appropriate color rendering.

In patent document U.S. Pat. No. 6,217,512, a portable visual cervical inspection apparatus for visual inspection of a cervix is disclosed. A light source is attached to the housing of the apparatus, adapted to illuminate the cervix with light such to enhance the definition between cancerous and healthy cervical tissue. To provide the illumination of the cervix, light-emitting diodes (LEDs) are used.

However, there are problems related to this invention. The lighting as disclosed in the mentioned patent document is not adequate for these purposes, as the light emitted by the combination of the LEDs does not provide a suitable color rendering.

SUMMARY OF THE INVENTION

It is an object of the present invention to provide a device that provides for an improved inspection of the cervix.

This and other objects are achieved by providing a portable device for cervical inspection having the features defined in the independent claim. Preferred embodiments are defined in the dependent claims.

According to the present invention, there is provided a portable device for cervical inspection, comprising an elongated housing having a first end, a second end, and an optical axis extending from the first end to the second end for allowing viewing through the housing, magnification means provided in the optical axis for providing a magnified view of a cervix for an observer observing the cervix by means of the portable device, a plurality of light-emitting diodes provided at the second end for illumination of cervical tissue, the plurality of light-emitting diodes comprising a first light-emitting diode group and a second light-emitting diode group, wherein the first light-emitting diode group emits light within a first wavelength range upon operation, and the second light-emitting diode group emits light within a second wavelength range upon operation, wherein the first wavelength range comprises or includes a sub-range of wavelengths shorter than the wavelengths of the second wavelength range, and the second wavelength range comprises or includes a sub-range of wavelengths longer than the wavelengths of the first wavelength range, the portable device further comprising a controller provided for a control of the luminous intensity of the second light-emitting diode group from a first intensity to a second intensity, lower than the first intensity, such that a preferred color rendering for the visual examination of the cervix may be provided.

Thus, the portable device of the present invention is based on the idea of providing an improved inspection of the cervix. The portable device provides the user, e.g. a doctor or a nurse, with a magnification of the cervix, and an illumination with an optimized lighting spectrum for obtaining a color rendering that is optimal for such examination. The plurality of LEDs are divided into two LED groups, wherein the first LED group emits light within a wavelength range different from the light emitted from the second LED group, upon operation of the portable device. By controlling the luminous intensity of the second LED group, the user may set the lighting for a preferred illumination mode which provides the appropriate color rendering necessary for each step during the visual inspection of the cervix.

The portable device of the present invention provides a light spectrum for increasing the sensitivity of the human eye to discriminate between normal tissue and pathological tissue, e.g. dysplastic changes in the epithelial mucosa. For that reason, lighting with an appropriate spectral range is provided for the visual examination of the cervix. Thus, the lighting of the portable device overcomes the deficiencies of conventional RGB LED combination lighting being inadequate for providing good color rendering.

The examiner (e.g. doctor, nurse or midwife) performing the inspection using the portable device may, in an initial phase of the inspection, use the full intensities of the first and the second LED groups to obtain a "normal" white light. Many examiners may prefer this normal light when orienting the device in the vagina or another body cavity. When the device is oriented (e.g. when the cervix is in focus), the examiner may control the long-wavelength light by reducing the intensity of the second LED group to obtain a light adapted for tissue inspection.

The portable device of the present invention may employ a red-reduced illumination, or "red-free" mode, obtained by reducing the intensity of the second LED group to reproduce the color rendering necessary for the second stage of visual inspection. In other words, a switching off, or dimming, of the long-wavelength light may reproduce a color rendering which is beneficial and which examiners are used to when performing visual inspection of the cervix.

Thus, the present invention discloses an improvement of cervical inspection compared to prior art.

By "portable device", it is here meant a device which is hand held, relatively small, easy to carry and to transport. As an example, the device may be portable in an ordinary bag, a pocket, or the like.

Although the portable device is foremostly intended for cervical inspection, i.e. inspection of the cervix, the portable device may be used for any other body cavity inspection such as e.g. observations of mucosal lesions in-situ. Such observations of mucosal lesions in-situ is necessary whenever insertion of the portable device into body cavity is to be avoided, for example due to discomfort or when contact with body liquids should be avoided due to risk of contamination, or whenever insertion is simply not required.

The portable device comprises an elongated housing, wherein the housing may be in the shape of a tube, a cylinder, or the like. The housing has a first end, a second end and an optical axis extending from the first end to the second end for allowing viewing through the housing, i.e. the ends are at least partially translucent such that a user may see through the housing. In other words, a user may see through the first end and the second end of the housing.

Furthermore, the portable device comprises magnification means provided in the optical axis for providing a magnified view of a cervix for an observer observing the cervix by means of the portable device. Thus, for a user, the cervix under inspection may be magnified such that an inspection of the cervix is made easier, more reliable and more convenient. The means for magnification may be a magnification lens, a plurality of lenses and/or mirrors and/or prisms, or any other means for magnification known in the art such that an enlarged view of the cervix is provided for the user of the portable device. The power of magnification may, for example, be 3×-20×.

A plurality of LEDs are provided at the second end of the housing for illumination of cervical tissue. In the case of a housing having the form of a tube or cylinder, the plurality of LEDs may be provided around the translucent part of the second end of the housing, e.g. at the circumference of the second end. The arrangement of LEDs may be such that the LEDs are evenly distributed, i.e. that the LEDs form a ring at the second end of the housing. Alternatively, the LEDs may be provided in clusters, i.e. arranged in groups. In such groups, the LEDs from the first LED group and the second LED group may be provided in the same cluster such that an even light distribution is provided.

As an example, there plurality of LEDs may be imply e.g. 10-30 LEDs that are arranged at the second end of the housing. The arrangement of LEDs may for example be three groups of LEDs with four adjacently provided LEDs in each group. As a further example, there may be four groups of LEDs with five adjacently provided LEDs in each group, or, alternatively, five groups of LEDs with five adjacently provided LEDs in each group.

By the expression "at the second end of the housing", it is meant that the plurality of LEDs are situated such that the light emitted from the LEDs upon operation of the portable device is directed mainly in the direction of the object to be inspected. In other words, the plurality of LEDs are provided such that the light is emitted away from an observer viewing through the portable device from the first end of the housing.

The plurality of LEDs comprises a first LED group and a second LED group, wherein the first LED group emits light within a first wavelength range upon operation, and the second LED group emits light within a second wavelength range upon operation. Thus, the plurality of LEDs are separated in terms of illumination wavelength such that some LED or LEDs emit light within a wavelength range whereas other LED or LEDs emit light in another wavelength range.

The first wavelength range comprises a sub-range of wavelengths shorter than the wavelengths of the second wavelength range. In other words, at least a portion of the first wavelength range is below at least a portion of the second wavelength range.

As an example, the first and the second wavelength range may be strictly separated, such that the longest wavelength of the first wavelength range is shorter than the shortest wavelength of the second wavelength range. In other terms, there is no "overlap" of the two ranges for this embodiment. As an numerical example of this, the first wavelength range may be provided below 620 nm, i.e. that the maximum wavelength of the first wavelength range may be shorter than 620 nm, whereas the second wavelength range may be provided above 620 nm, i.e. that the minimum wavelength of the second wavelength range may be longer than 620 nm.

As a further example, the first and the second wavelength range may be provided such that a portion of the first wavelength range comprises wavelengths longer than wavelengths comprised in the second wavelength range. In other terms, there may be an "overlap" of the two ranges. As an numerical example of this, the first wavelength range may be provided up to 650 nm, i.e. that the maximum wavelength of the first wavelength range may be 650 nm, whereas the second wavelength range may be provided from 580 nm, i.e. that the minimum wavelength of the second wavelength range may be 580 nm.

Accordingly, the second wavelength range may comprise a sub-range of wavelengths longer than the wavelengths of the first wavelength range, i.e. that the second wavelength range comprises a portion wherein the wavelengths are longer than those wavelengths comprised in the first wavelength range.

As a further example, the first and the second wavelength range may be provided such that the LED group with the shorter wavelength (i.e. the first LED group) generates a red-free spectral power distribution and the LED group that includes the longer wavelength (i.e. the second LED group) generates a visible spectral power distribution of a white halogen light. Accordingly, alternating between the two different LED groups can equivalently generate the two modes of illumination for colposcopic examination, i.e. illumination with the visible spectrum of white halogen light or illumination with a red-free visible spectrum.

The portable device further comprises a controller provided for a control of the luminous intensity of the second LED group from a first intensity to a second intensity, lower than the first intensity.

By the word "controller", it is here meant a switch, knob, lever, or the like for the control of the luminous intensity. As an example, in case of a switch, the luminous intensity of the of the second LED group is switched from a first intensity to a second intensity. Hence, by simply applying the switch, the second intensity of the second LED group is rendered. As another example, the controller may be a knob, a lever, a dimmer, or the like, such that the user may regulate the luminous intensity continuously from a first intensity to a second intensity. In other words, the user may dim or fade the lighting from a first intensity to a second intensity.

The control of the luminous intensity is provided for the second LED group from a first intensity to a second intensity, lower than the first intensity. Thus, the user may switch, dim or fade the lighting of the second LED group such that the luminous intensity of the second LED group becomes lower than the luminous intensity from the first LED group upon operation of the portable device.

Thus, the controller may enable at least two stages of illumination. In the first stage of illumination, the intensity of the first LED group and the first intensity of the second LED group may provide a first stage illumination. In the second stage of illumination, the intensity of the first LED group and the second intensity of the second LED group may provide a "red-reduced" illumination.

Thus, by controlling the luminous intensity of the second LED group, the user may switch the lighting from e.g. a general examination mode, which may be white light, to e.g. a dysplasia-sensitive mode, which may be free from red, or red-reduced, and vice versa. The advantage of this is discussed above.

The simple operation of the controller of the portable device facilitates the illumination setting, which especially is important for the use of the portable device in rural areas, outdoor environments or in environments with limited electricity resources.

Another advantage of the portable device is when appropriate legal documentation of sexual abuse is needed but access to conventional colposcope is limited or does not exist.

Thus, this invention provides a portable device for cervical inspection which is supple, efficient, easy to use and may provide a color rendering that enables the user to conveniently perform reliable cervical examination. The features of the portable device describe how to reliably produce color rendering suitable for visual inspection of pre-cancerous lesions in the cervix in-situ.

According to an embodiment of the present invention, white light is generated by the device upon operation when the first intensity of the second light-emitting diode group is used. Thus, white light may be rendered from the first light-emitting diode group and the second light-emitting diode group, before the luminous intensity of the second LED group is further controlled.

According to an embodiment of the present invention, the second luminous intensity is 0-40%, such as 5-35%, such as 10-30%, such as 15-25%, such as about 20% of the luminous intensity of the first luminous intensity. Preferably, the first luminous intensity is the intensity of the second LED group that is necessary to reach white balance with the first LED group. In such case, white light is thus obtained when, during operation, the second LED group emits light of the first intensity.

By dimming or diminishing the orange to red light emitted by the second LED group to substantially 20% of the luminous intensity of the first luminous intensity, the illumination enables a higher sensitivity for visual detection of pre-cancerous changes in the cervical mucosa.

Thus, this portion of the previous luminous intensity is considered to further enhance the conditions for an improved cervical inspection. The luminous intensity relation between the first and the second LED groups, being approximately 5:1, after the switching, dimming or fading of the luminous intensity of the second LED group, facilitates the inspection for the user. This is realized as the luminous intensity of the first LED group, with a wavelength range different to the wavelength range of the second LED group, dominates the illumination upon examination. Thus, the wavelengths of the light which are more susceptible to render a preferred illumination regarding cervix observation, dominates over the wavelengths of the light which may affect the illumination negatively, i.e. a deterred illumination for the purpose of cervix inspection.

According to an embodiment of the present invention, the first wavelength range is within 400-650 nm, such as within 425-625 nm, and the second wavelength range is within 580-700 nm, such as within 600-670 nm.

Thus, the first wavelength range may emit visible light within the range from violet to orange/red, i.e. 400-650 nm, whereas the second wavelength range may emit visible light in the range from yellow to red, i.e. 580-700 nm. More specifically, the first wavelength range may emit visible light within the range from violet to orange (425-625 nm), whereas the second wavelength range may emit visible light within the range from orange to red (600-700 nm).

In other terms, the color rendering of the LEDs may be arranged such that the first LED group emits light substantially in the colors violet to orange, whereas the second LED group emits light substantially in the colors orange to red. Thus, the light emitted upon operation of the portable device is substantially separated in terms of color.

Dimming or switching off the luminous intensity of the orange to red light emitted by the second LED group upon operation of the portable device implies a domination of the violet to orange light, emitted by the first LED group. The controller lets the user dim, or switch off, the substantially orange to red light such that the color of the light emitted by the LEDs of the first and the second LED groups is dominated by the luminous intensity of the light with shorter wavelengths. This is advantageous, as this setting of the light provides a light which is more suitable for inspection of mucosal tissue such as cervical tissue.

The control of the second LED group enables the user to adjust the illumination to be optimal for his or her experience regarding cervical inspection.

By switching, dimming or fading the second luminous intensity of the orange to red light emitted by the second LED group to substantially 20% of the luminous intensity of the first luminous intensity, the illumination switches from a "white light mode" to a "red-reduced mode", which provides an improved visual identification of certain lesions and is therefore improves the visual examination of the cervix. The LED group emitting violet to orange light with a luminous intensity approximately five times higher than the luminous intensity of the LED group emitting orange to red light, provides a illumination setting which is preferred for the visual examination of the cervix.

According to an embodiment of the present invention, the range for the at least one peak of the light within the first wavelength range is 425-625 nm, such as 450-575 nm and the range for the at least one peak of the light within the second wavelength range is 600-670 nm, such as 620-670 nm.

According to an embodiment of the present invention, the first LED group comprises three LEDs and the second LED group comprises one LED, wherein the three diodes of the first LED group have peak wavelengths of 460-480 nm, 500-520 nm and 545-565 nm, respectively, and wherein the diode of the second LED group has a peak wavelength of 650-670 nm. Thus, the peaks corresponding to the wavelengths of the three LEDs of the first LED group emits a blue, a blue/green and a green light, respectively, whereas the peak corresponding to the wavelength of the diode of the second LED group emits a red light.

By this selection of wavelengths of the LEDs of the first and the second LED groups, the spectral power distribution of the LEDs is optimized, and therefore advantageous for the visual inspection of the cervix. Due to the provision of the LEDs of the first LED group, the individual spectral power distributions give rise to an overlap of luminous intensities such that instead of separate spectral power distributions, the LEDs provide a continuous spectral power distribution approximately between 425 and 625 nm. By providing a spectral power distribution wherein the first LED group emits light which is continuous at least within 425-625 nm, an even further improved rendering of light for the visual inspection of the cervix may be provided. By providing a light during operation of the portable device which is continuous at least within 425-625 nm, the lighting may even further improve the conditions for a visual inspection of the cervix e.g. compared to light settings providing discontinuous light in this range. For example, light settings with (few) LEDs having narrow spectrums, such that the light becomes discontinuous within 425-625 nm, may not be adequate for the purposes of cervical inspection, as the light thereby may not provide a suitable color rendering.

The spectral power distribution of the second LED group yields a distribution which is substantially separated from the distribution resulting from the first LED group upon operation of the portable device. The spectral power distribution of the light emitted from the first LED group becomes "smeared", i.e. a smooth transition between the three peaks, whereas for the single diode, only one peak is defined.

According to an embodiment of the present invention, the luminous intensity of the second diode of the first LED group is 40-60%, such as about 50% higher than the luminous intensity of the first diode of the first LED group, and the luminous intensity of the third diode of the first LED group is 20-30%, such as about 25% higher than the luminous intensity of the first diode of the first LED group. In other terms, the ratio of luminous intensity between the three diodes of the first LED group is approximately 4:6:5.

According to an embodiment of the present invention, the first LED group comprises four LEDs and the second LED group comprises one LED, wherein the four diodes of the first LED group have peak wavelengths of about 460-480 nm, 495-515 nm, 515-535 nm and 545-565 nm, respectively, and wherein the diode of the second LED group has a peak wavelength of 615-635 nm. Thus, there are four peaks corresponding to the wavelengths from the four diodes of the first LED group and one peak corresponding to the wavelength from the diode of the second LED group. As the interval between adjacently provided LEDs in the first LED group is decreased, in terms of wavelength, the spectral power distribution within the wavelength range becomes more even, as the more narrowly provided peaks "bridge" even more smoothly between each other.

According to an embodiment of the present invention, the luminous intensity of the second diode of the first LED group is 40-60%, such as about 50% lower than the luminous intensity of the first diode of the first LED group, the luminous intensity of the third diode of the first LED group is substantially 40-60%, such as about 50% lower than the luminous intensity of the first diode of the first LED group, and the luminous intensity of the fourth diode of the first LED group is 90-110%, such as about the same as the luminous intensity of the first diode of the first LED group. In other terms, the ratio of luminous intensity between the four diodes of the first LED group is approximately 2:1:1:2.

As an alternative, the first LED group and the second LED group may be incorporated into a LED lamp, thereby essentially producing the illumination effects disclosed above. Examples of such lamps are comprised in Very-High-Luminosity (VHL) Chip-on-Board (COB) technologies.

According to an embodiment of the present invention, the first light-emitting diode group comprises one light-emitting diode having a peak wavelength of about 505-535 nm. Thus, the peak of luminosity corresponds to a wavelength of about 505-535 nm. As an example, the light-emitting diode may have a peak wavelength of about 520 nm and the luminous intensity throughout the range 505-535 nm may be ≥50% of the peak luminous intensity. In other words, within 505-535 nm, the luminous intensity may be more than half of the maximum luminous intensity in that range.

This wavelength range has a specific advantage for deuteranomalic persons, which is the most common green color-blindness and which approximately affects 5% of the males. This color may be better distinguished by deuteranomatic persons than other colors in the green/yellow color range. Therefore, this specific wavelength range enables deuteranomalic examiners to utilize better the effect of the green filter and therefore improve their suboptimal capability to recognize cervical lesions and abnormal vascular pattern.

According to an embodiment of the present invention, the portable device further comprises at least one collimating means. By this, the light from the first light-emitting diode group and the light from the second light-emitting diode group may be collimated, i.e. parallelly aligned. In this way, the light may be homogenized.

According to an embodiment of the present invention, the portable device further comprises at least one optical fiber such that the light from the first light-emitting diode group and the light from the second light-emitting diode group is guided through the at least one optical fiber. By means of the at least one optical fiber, the light from the LEDs may guided such that the light is homogenized.

According to an embodiment of the present invention, the portable device further comprises at least one means of polarization.

According to an embodiment of the present invention, the portable device further comprises at least one means arranged for a display of the view of the cervix. The term "display" should in this context be construed broadly, as the term here means a presentation of information. Thus, the at least one means arranged for a display of the view of the cervix may comprise an optical interface, e.g. a screen such that the view of the cervix may be presented contemporary to e.g. a number of doctors and/or nurses.

Thus, the at least one means for the display of the view of the cervix has the advantage that not only the person operating the portable device may view and/or construe the view of the cervix, but also that other persons such as doctors and/or nurses may be present at the inspection and take part of the inspection of the cervix.

The at least one means for the display of the view of the cervix may be either analogue, i.e. the at least one means may display the view of the cervix by projection on a screen, e.g. a film screen, or digital, i.e. that the at least one means may display the view of the cervix on e.g. a computer screen or a digital display.

According to an embodiment of the present invention, the portable device further comprises at least one means for registration of the view of the cervix. By "registration", it is here meant e.g. recording or storing such that the view of the cervix may be inspected and/or shown at a later occasion. An advantage with the at least one means for registration of the view of the cervix is that the information from the view of the cervix may be documented for the purpose of clinical documentation and/or for legal documentation of sexual abuse.

Thus, in the case of clinical documentation, the at least one means for registration of the view of the cervix may improve any kind of clinical analysis, such as e.g. comparisons between inspections and/or statistical analysis. In the case of documentation of sexual abuse, the at least one means for registration of the view of the cervix may serve as a tool in investigations of e.g. rape, sexual assault and related genital injury.

As a further example, the at least one means for registration of the view of the cervix may form a part of a kit addressing sexual abuse documentation. By this, it is meant that the means for registration may improve any documentation of sexual abuse by forming a device which may be used, by itself or on combination with other devices, as a tool of documentation.

The means for registration of the view of the cervix may, as an example, be a means for registration of the cervix images, e.g. a camera such as a photographic camera or a television camera. Thus, a view or views of the cervix may be registered as a sampled image or images, or as a film. Alternatively, the means for registration of the view of the cervix may be a digital memory, e.g. a hard disk or a memory stick, such that the view or views of the cervix is stored or saved digitally.

As a further example, the portable device may further comprise at least one means arranged for a display of the view of the cervix and at least one means for registration of the view of the cervix. By this, it is meant that the view of the cervix that may be displayed also is registered. As an example, the view of the cervix which may be presented on e.g. a screen may at the same time be registered by a recording such as e.g. a video, a film and/or a digital recording.

According to an embodiment of the present invention, the portable device further comprises optical means arranged for increasing the thickness of the focal plane of the portable device (i.e. an increase of the depth of focus; DoF), thereby increasing the tolerance for a variation in position of the portable device upon operation. In other words, in this embodiment of the invention, the portable device comprises optical means to keep the cervix in focus during operation of the portable device, although the portable device may be subjected to variation in position due to e.g. shaking, trembling and/or tremors when holding the portable device. Thus, the optical means provide the advantage of providing/maintaining the focus of the cervix under inspection, even though the portable device is hand held during operation, and thereby, possibly, being subjected to deviations in position. Hence, the optical means arranged for increasing the thickness of the focal plane even further improves the cervical inspection.

Moreover, the optical means arranged for increasing the thickness of the focal plane may employ a curved focal plane which is adapted to the curvature of the cervix. Furthermore, the optical means may provide an increased exit pupil, i.e. increase the size of the image to the pupil(s) of the examiner during inspection of the cervix. The optical means thereby even further ameliorate the cervical inspection by the examiner.

BRIEF DESCRIPTION OF THE DRAWINGS

These and other aspects of the present invention will now be described in more detail, with reference to the appended drawings showing a currently preferred embodiment of the invention, wherein.

DETAILED DESCRIPTION

In the following description, the present invention is described with reference to a portable device for cervical inspection.

Figure 1:
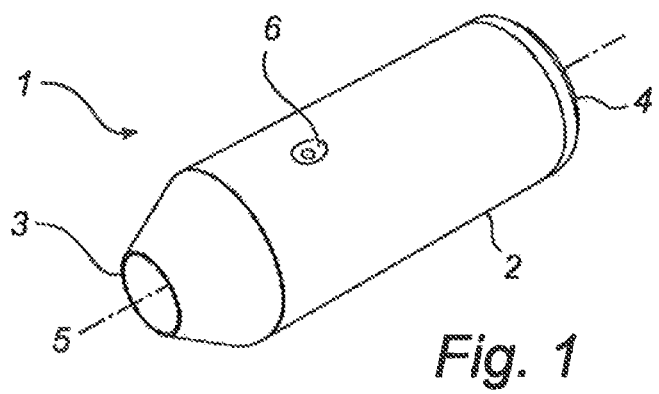
FIG. 1-2 show the portable device according to an exemplifying embodiment of the present invention.

FIG. 1 shows the portable device 1 according to an exemplifying embodiment of the present invention. The portable device 1 comprises an elongated housing 2 in the shape of a cylinder, having a first end 3 and a second end 4. At the first end 3, the elongated housing 2 is beveled such that the cross section of the first end 3 is smaller than the cross section of the second end 4. For the convenient use and cleaning of the portable device 1, e.g. such that the portable device 1 is easy to disinfect, the elongated housing 2 comprises a waterproof plastic material.

An optical axis 5 extends from the first end 3 to the second end 4 of the elongated housing 2. The optical axis 5 allows a user to view through the elongated housing 2 from the first end 3, to investigate a cervix provided beyond the second end 4. Magnification means (not shown) are provided in the optical axis 5, preferably close to the second end 4, for providing the observer/examiner with a magnified view of a cervix. Furthermore, optical means with a sufficient DoF (not shown) may be provided, arranged for a tolerance of changes/deviations in position of the portable device 1 due to possible shaking/trembling of the examiner's hand during inspection. A switch 6 for the lighting (not shown) is press fit on the upper portion of the elongated housing 2, whereas the lighting is provided by batteries (not shown).

Figure 2:
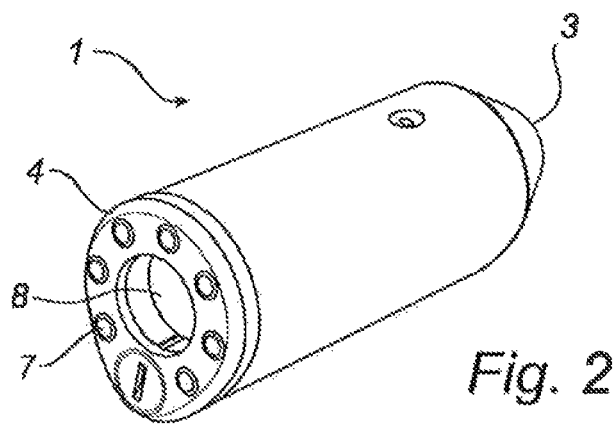

In FIG. 2, the portable device 1 is shown from a reversed angle compared to FIG. 1. At the second end 4 of the elongated housing 2, a plurality of LEDs 7 are provided for the illumination of cervical tissue. The LEDs 7 are evenly distributed in a circle at the second end 4, around the aperture of the elongated housing 2 at the second end 4. The magnification means 8, depicted here as a lens, a part of a binocular, a part of a monocular or a part of a microscope, is provided at the second end 4.

Figure 3A:
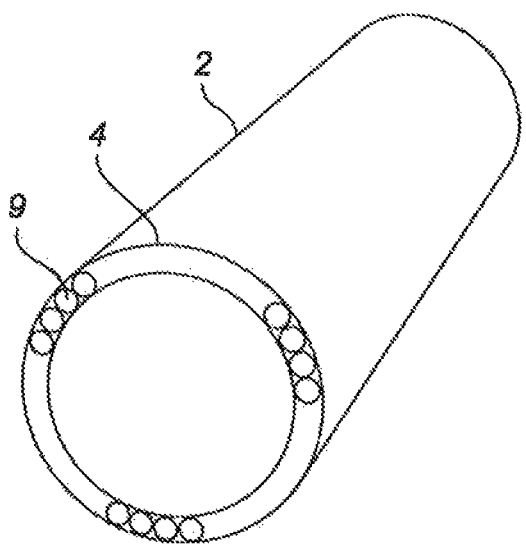
FIG. 3 shows perspective views of the elongated housing and the LEDs provided at the second end of the elongated housing according to exemplifying embodiments of the present invention.

FIG. 3a shows the elongated housing 2 of the portable device 1, wherein the elongated housing 2 is shaped as a cylinder. A plurality of LEDs 9 are provided around the second end 4 of the elongated housing 2, at the circumference of the second end 4. The twelve LEDs 9 of this embodiment are provided in three groups of LEDs, the three groups being evenly distributed around the circumference, each group having four adjacently provided LEDs. The four LEDs of each group are provided after each other, along a sector of the circumference of the second end 4.

Figure 3B:
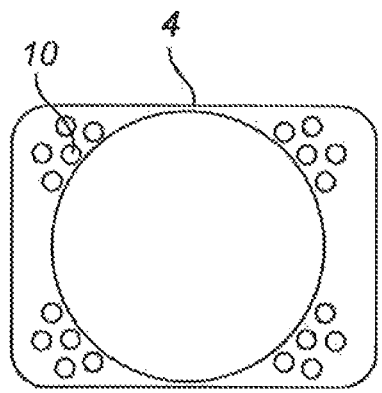

In FIG. 3b, the elongated housing 2 has an inner cross section, which is circular-shaped, and an outer cross section, which is rectangular-shaped. At this circumference of the second end 4 of the elongated housing 2, there are four evenly distributed groups of LEDs 10, each group provided in the vicinity of the corners of the rectangle of the cross-section. Each group of LEDs consists of five adjacently provided LEDs.

Figure 3C:
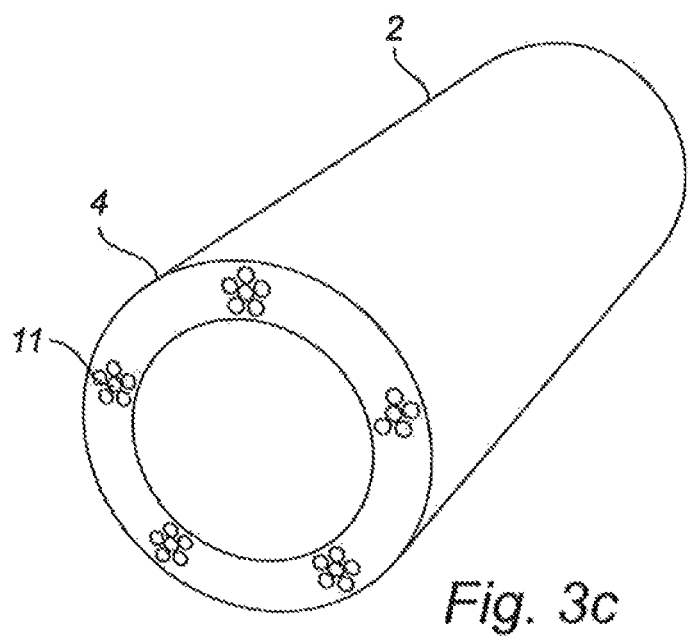

In FIG. 3c, the elongated housing 2 of the portable device is shaped as a cylinder, but with a somewhat thicker cylinder wall than of that elongated housing 2 depicted in FIG. 3a. At the circumference of the second end 4 of the elongated housing 2, there are five evenly distributed groups of LEDs 11, each group of LEDs consisting of five adjacently provided LEDs.

Although FIGS. 3a-3c show group of LEDs with a specific number of LEDs which are provided symmetrically at the second end 4 of the elongated housing 2, is understood that these serve as exemplifying embodiments only, and that other arrangements of LEDs may be feasible embodiments.

Figure 4:
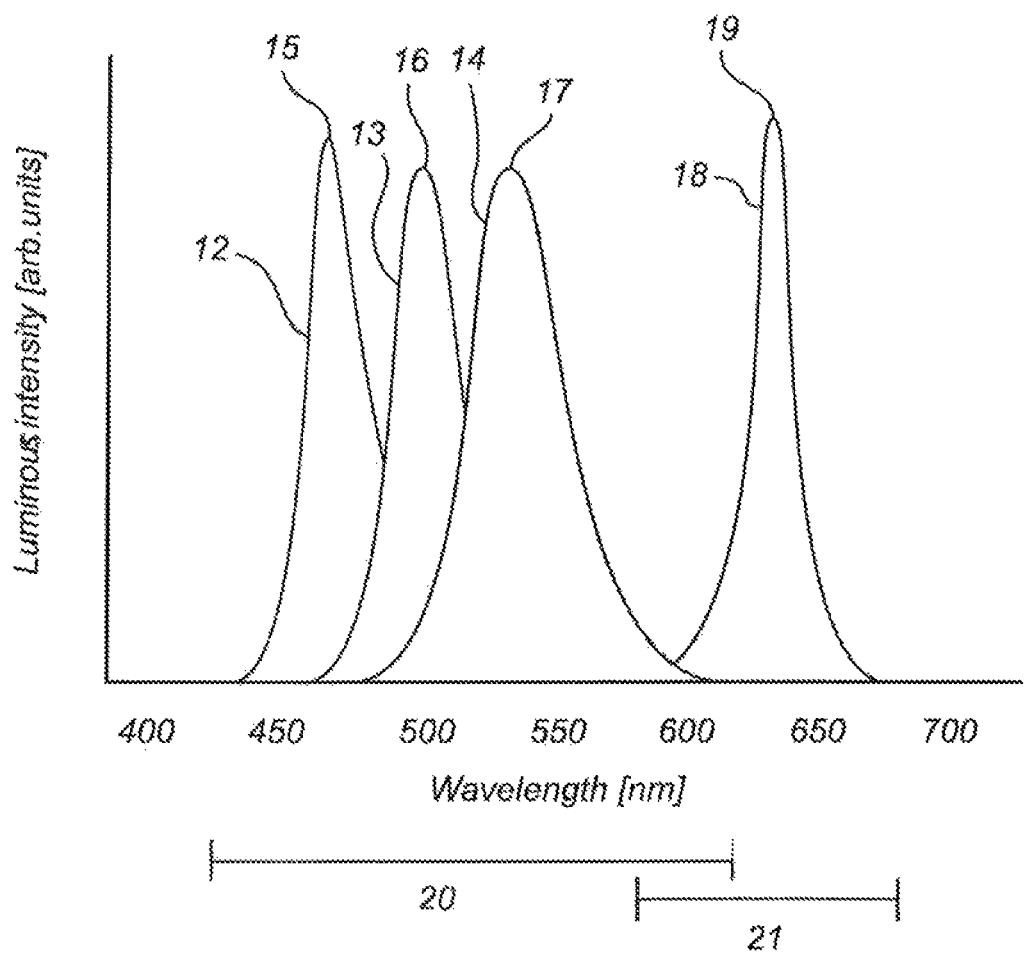
FIG. 4 shows the luminous intensity, in arbitrary units, as a function of wavelength

In FIG. 4, the luminous intensity, in arbitrary units, is shown as a function of wavelength, in nanometers (nm). The three leftmost luminous intensity distributions 12, 13, and 14, respectively, show the light as emitted by the first LED group, which may comprise three LEDs. The three diodes have peaks at wavelengths about 470 nm, 510 nm and 540 nm, respectively, shown as 15, 16, and 17, respectively, in FIG. 1.

The luminous intensity distribution 12-14 of each of the LEDs upon operation resembles that of a Gauss-bell or normal distribution, such that the luminous intensity in the vicinity of the peaks 15-17 decreases rapidly, whereas the luminous intensities for wavelengths further away from the peaks 15-17 decrease more slowly.

The width for the power distribution 12 represented by the peak 15 at the wavelength 470 nm and the width for the distribution 13 represented by the peak 16 at the wavelength 510 nm, are approximately the same, whereas the width for the power distribution 14 represented by the peak 17 at the wavelength 540 nm is somewhat greater.

Together, the three LEDs of the first LED group emit light in the range 20 of approximately 425-625 nm. Furthermore, the luminous intensity distribution of the light emitted from the first LED group becomes overlapped, i.e. there is a transition between the three distributions 12-14 such that in the spectral range of the light emitted from the three LEDs, the luminous intensity is above zero throughout the entire range.

The intensity maximum of the distribution 12, represented by the peak 15 at the wavelength 470 nm, is somewhat greater than the intensity maximums of the distributions 13 and 14 represented by the peaks 16 and 17 at wavelengths 510 and 540 nm, respectively, being approximately the same.

The rightmost luminous intensity distribution 18 is the light which may be emitted by one or more diodes in the second LED group. The wavelength of its peak 19 is about 630 nm, whereas the distribution 18, analogously to the three leftmost distributions, is bell-shaped. The width of the rightmost distribution 18 is comparable to that of the two leftmost distributions 12 and 13, whereas the luminous peak intensity 19 is somewhat greater than the intensities 15-17 of the three leftmost distributions 12-14.

The diode of the second LED group emits light in the range 21 of approximately 580-670 nm. Thus, there is a small overlap of light with wavelengths between 580-625 nm for the ranges 20 and 21.

Although the description of FIG. 4 refers to three diodes of the first LED group and one diode of the second LED group, any number of LEDs in the first and the second groups may be feasible embodiments for the approximate reproduction of the luminous intensity as shown.

Figure 5:
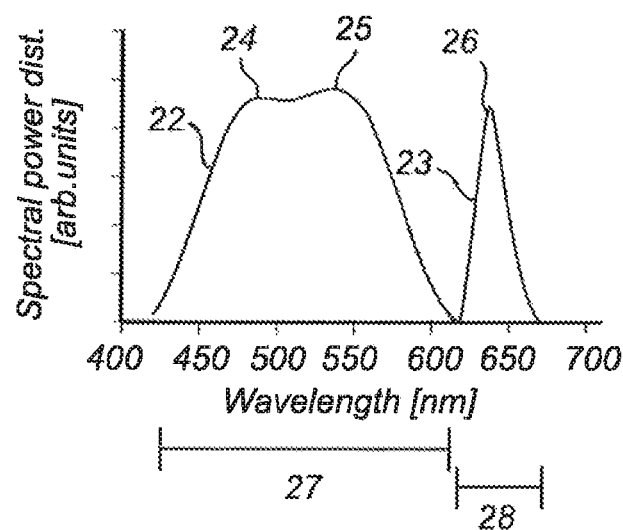
FIG. 5-6 show the spectral power distribution of the LEDs, in arbitrary units, as a function of wavelength.

FIG. 5 shows an example of the spectral power distribution of the LEDs, in arbitrary units, as a function of wavelength, in nanometers (nm). The LEDs of the first LED group have a spectral power distribution 22 for the wavelength range 27 of approximately 425-620 nm, whereas the second LED group has a spectral power distribution 23 for the wavelength range 28 of approximately 625-670 nm. Thus, the spectral power distribution 22 for the first LED group is wider and not as sharp as the spectral power distribution 23 for the second LED group. Furthermore, the two ranges 27 and 28 indicate that the spectral power distribution is separated between light with shorter wavelengths and light with longer wavelengths. In the example, the spectral power distribution is designed to mimic the spectral power distribution of daylight. However, other preferred embodiments could be feasible, e.g. in that the spectral power distribution imitates a black body spectral power distribution of a conventional halogen lamp, within the visible spectrum.

Furthermore, the spectral power distribution 22 for the first LED group shows two peaks, with one peak 24 at approximately 480 nm and the second peak 25 at approximately 540 nm, both peaks 24 and 25 having approximately the same spectral power at these wavelengths. For the second LED group, the single peak 26 is almost as high as two the peaks 24 and 25 for the first LED group, the peak 26 being found at approximately 640 nm.

Figure 6:
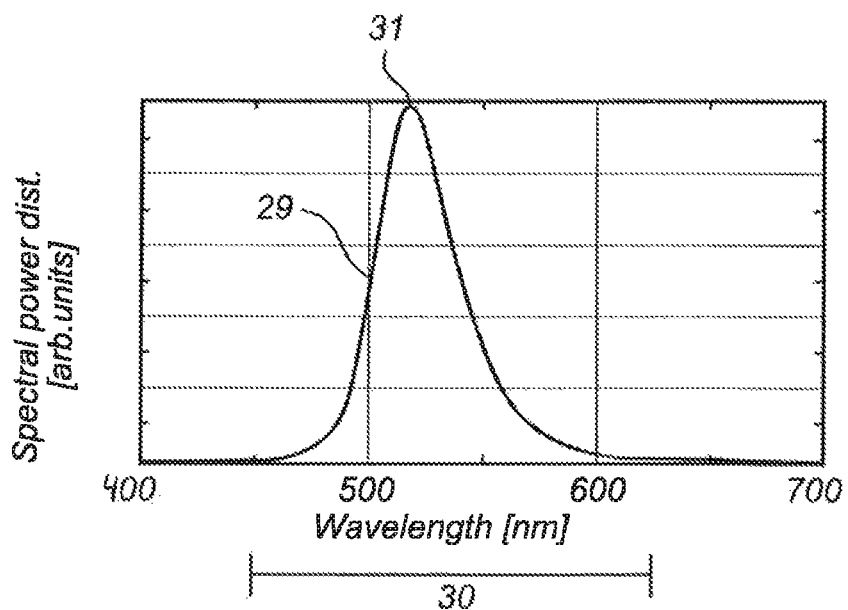

FIG. 6 shows the spectral power distribution of the first group of LEDs, in arbitrary units, as a function of wavelength, in nanometers (nm). The LEDs of the first LED group have a spectral power distribution 29 for the wavelength range 30 of approximately 450-625 nm, and the peak wavelength 31 is approximately 520 nm. Whereas the spectral power distribution in FIG. 5 for the first group of LEDs may be rendered by a plurality of LEDs, the spectral power distribution 29 in FIG. 6 may be rendered by a single diode.

Even though the invention has been described with reference to specific exemplifying embodiments thereof, many different alterations, modifications and the like will become apparent for those skilled in the art. The described embodiments are therefore not intended to limit the scope of the invention, as defined by the appended claims.

For example, the elongated housing 2 may take on any other shape than the elongated tube or cylindrical shape described such that the invention still renders the features referred to. This also holds for the means for magnification such as a magnification lens, as any other any means for yielding a magnification of the view of the cervix is possible.

Furthermore, wavelength described numerically in this detailed description should not be construed exactly, but more serve as an indication of a wavelength data. As an example, a wavelength of x may perfectly well be realized as a wavelength within e.g. 5% of that wavelength x, i.e. 0.95x-1.05x.

Moreover, the colors referred to should be construed as a translation of the numerical data of the wavelengths into the more easily referable portion of the visible light. As an example, the wavelength of 650 nm is translated to the colors orange/red, whereas the interpretation of which wavelength of the visible light represents the color transition orange/red, is more subjective to the viewer.

The controller, with which the user may switch off, dim or fade the luminous intensity of the second LED group, is exemplified as a switch, knob, lever, dimmer, or the like. However, any other means for the discrete or continuous control of the luminous intensity such as a dial, a button, a device for sliding control, a finger-sensing pad, or the like may just as well be feasible realizations of the control.

The invention claimed is:

1. A portable device for inspection of a portion of a body comprising:
   an elongated housing having a first end, a second end, and an optical axis that extends from the first end to the second end that allows viewing through the elongated housing;
   a magnification element that lies in the optical axis, wherein said magnification element is configured to provide a magnified view of a portion of a body to an observer observing the portion of the body with the portable device;

a plurality of light-emitting diodes located at the second end and configured to illuminate the portion of the body, the plurality of light-emitting diodes comprising a first light-emitting diode group and a second light-emitting diode group, wherein the first light-emitting diode group emits light within a first wavelength range upon operation, wherein the light is continuous at least within 425-625 nm, and the second light-emitting diode group emits light within a second wavelength range upon operation, wherein the first wavelength range comprises a sub-range of wavelengths shorter than the second wavelength range, the second wavelength range comprises a second sub-range of wavelengths longer than the first wavelength range, and the first light-emitting diode group comprises three light-emitting diodes and the second light-emitting diode group comprises one light-emitting diode, wherein the three light-emitting diodes of the first light-emitting diode group have peak wavelengths of about 470 nm, 510 nm and 555 nm, respectively, and wherein the light-emitting diode of the second light-emitting diode group has a peak wavelength of about 660 nm; and a controller provided configured to control a luminous intensity of the second light-emitting diode group from a first intensity to a second intensity that is lower than the first intensity, to provide a preferred color rendering for visual examination of the portion of the body.

2. The portable device as claimed in claim 1, wherein white light is generated by the portable device during operation when the first intensity of the second light-emitting diode group is used.

3. The portable device as claimed in claim 1, wherein the second intensity of the second light-emitting diode group is selected from 0-40%, 5-35%, 10-30%, 15-25%, or about 20% of the luminous intensity of the first luminous intensity.

4. The portable device as claimed in claim 1, wherein the first wavelength range is within 400-650 nm, or within 425-625 nm, and the second wavelength range is within 580-700 nm, or within 600-670 nm.

5. The portable device as claimed in claim 4, wherein a range for at least one peak of the light within the first wavelength range is 425-625 nm, or 450-575 nm and the range for the at least one peak of the light within the second wavelength range is 600-670 nm, or 620-670 nm.

6. The portable device as claimed in claim 1, wherein luminous intensity of the second diode of the first light-emitting diode group is about 50% higher than the luminous intensity of the first diode of the first light-emitting diode group, and the luminous intensity of the third diode of the first light-emitting diode group is about 25% higher than the luminous intensity of the first diode of the first light-emitting diode group.

7. The portable device as claimed in claim 1, further comprising at least one collimating element.

8. The portable device as claimed in claim 1, further comprising at least one optical fiber such that the light from the first light-emitting diode group and the light from the second light-emitting diode group is guided through the at least one optical fiber.

9. The portable device as claimed in claim 1, further comprising at least one polarization element.

10. The portable device as claimed in claim 1, further comprising at least one display element configured to display a view of a cervix.

11. The portable device as claimed in claim 1, further comprising at least one registration element configured to register a view of a cervix.

12. The portable device as claimed in claim 1, further comprising at least one optical element configured to increase a thickness of a focal plane of the portable device.

13. The portable device as claimed in claim 1, wherein said portion of said body is a cervix.

14. The portable device as claimed in claim 1, wherein said portion of said body is a body cavity.

15. The portable device as claimed in claim 1, wherein said portion of said body is tissue.

16. A portable device for inspection of a portion of a body comprising:

an elongated housing having a first end, a second end, and an optical axis that extends from the first end to the second end that allows viewing through the elongated housing;

a magnification element that lies in the optical axis, wherein said magnification element is configured to provide a magnified view of a portion of a body to an observer observing the portion of the body with the portable device;

a plurality of light-emitting diodes located at the second end and configured to illuminate the portion of the body, the plurality of light-emitting diodes comprising a first light-emitting diode group and a second light-emitting diode group, wherein the first light-emitting diode group emits light within a first wavelength range upon operation, wherein the light is continuous at least within 425-625 nm, and the second light-emitting diode group emits light within a second wavelength range upon operation, wherein the first wavelength range comprises a sub-range of wavelengths shorter than the second wavelength range, the second wavelength range comprises a second sub-range of wavelengths longer than the first wavelength range, and the first light-emitting diode group comprises four light-emitting diodes and the second light-emitting diode group comprises one light-emitting diode, wherein the four light-emitting diodes of the first light-emitting diode group have peak wavelengths of about 470 nm, 505 nm, 525 nm and 555 nm, and wherein the light-emitting diode of the second light-emitting diode group has a peak wavelength of about 625 nm; and, a controller provided configured to control a luminous intensity of the second light-emitting diode group from a first intensity to a second intensity that is lower than the first intensity, to provide a preferred color rendering for visual examination of the portion of the body.

17. The portable device as claimed in claim 16, wherein luminous intensity of the second diode of the first light-emitting diode group is about 50% lower than the luminous intensity of the first diode of the first light-emitting diode group, the luminous intensity of the third diode of the first light-emitting diode group is about 50% lower than the luminous intensity of the first diode of the first light-emitting diode group, and the luminous intensity of the fourth diode of the first light-emitting diode group is about the same as the luminous intensity of the first diode of the first light-emitting diode group.

18. The portable device as claimed in claim 16, wherein white light is generated by the portable device during operation when the first intensity of the second light-emitting diode group is used.

19. The portable device as claimed in claim 16, wherein the second intensity of the second light-emitting diode group is selected from 0-40%, 5-35%, 10-30%, 15-25%, or about 20% of the luminous intensity of the first luminous intensity.

20. The portable device as claimed in claim 16, wherein the first wavelength range is within 400-650 nm, or within 425-625 nm, and the second wavelength range is within 580-700 nm, or within 600-670 nm.

21. The portable device as claimed in claim 20, wherein a range for at least one peak of the light within the first wavelength range is 425-625 nm, or 450-575 nm and the range for the at least one peak of the light within the second wavelength range is 600-670 nm, or 620-670 nm.

22. The portable device as claimed in claim 16, further comprising at least one collimating element.

23. The portable device as claimed in claim 16, further comprising at least one optical fiber such that the light from the first light-emitting diode group and the light from the second light-emitting diode group is guided through the at least one optical fiber.

24. The portable device as claimed in claim 16, further comprising at least one polarization element.

25. The portable device as claimed in claim 16, further comprising at least one display element configured to display a view of a cervix.

26. The portable device as claimed in claim 16, further comprising at least one registration element configured to register a view of a cervix.

27. The portable device as claimed in claim 16, further comprising at least one optical element configured to increase a thickness of a focal plane of the portable device.

28. The portable device as claimed in claim 16, wherein said portion of said body is a cervix.

29. The portable device as claimed in claim 16, wherein said portion of said body is a body cavity.

30. The portable device as claimed in claim 16, wherein said portion of said body is tissue.

* * * * *